United States Patent [19]

Wardwell

[11] 4,296,179

[45] Oct. 20, 1981

[54] FRANGIBLE BONDING USING BLUSH LACQUER

[76] Inventor: Charles R. Wardwell, 559 Oak St., Winnetka, Ill. 60093

[21] Appl. No.: 625,506

[22] Filed: Oct. 24, 1975

Related U.S. Application Data

[62] Division of Ser. No. 482,436, Jun. 24, 1974, Pat. No. 3,938,659.

[51] Int. Cl.³ .......................... B32B 9/06; C09J 7/02; A61B 17/06
[52] U.S. Cl. ................... 428/498; 428/200; 428/211; 428/212; 428/347; 428/354; 156/344; 206/439; 206/484
[58] Field of Search ............... 206/439, 484, 469, 498; 229/66; 156/254, 344, 277, 306; 428/40, 195, 200, 202, 211, 212, 304, 347, 352, 354, 498; 40/2 R

[56] References Cited

U.S. PATENT DOCUMENTS

| | | | |
|---|---|---|---|
| 2,477,196 | 7/1949 | Mohr | 156/254 |
| 2,939,802 | 6/1960 | Werle et al. | 428/476 |
| 2,957,791 | 10/1960 | Bechtold | 428/220 |
| 3,020,172 | 2/1962 | Mohnhaupt | 428/336 |
| 3,174,889 | 3/1965 | Anderson et al. | 156/254 |
| 3,527,400 | 9/1970 | Shepherd et al. | 206/498 |
| 3,595,468 | 7/1971 | Repko | 229/66 |
| 3,675,844 | 7/1972 | Sorrell | 428/40 |
| 3,753,841 | 8/1973 | Wheeler | 428/40 |
| 3,938,659 | 2/1976 | Wardwell | 206/439 |

FOREIGN PATENT DOCUMENTS 1953246  5/1970  Fed. Rep. of Germany ...... 156/344

Primary Examiner—William R. Dixon, Jr.
Attorney, Agent, or Firm—Fitch, Even, Tabin, Flannery & Welsh

[57] ABSTRACT

A frangible bonding system utilizes blush lacquer as the frangible link in a system for bonding a substrate to a surface, such as the surface of a cover layer. The system is particularly adapted for packaging sterilized products. A substrate, such as paper, is coated with a layer of blush lacquer and dried. An adhesive, such as heat seal material, is superposed. A cover layer is overlaid, with a product between the layers. The package is then sealed and sterilized. Opening of the package is by peeling the cover layer and substrate from one another, breaking the cohesive internal bonds of the blush lacquer.

3 Claims, 4 Drawing Figures

FRANGIBLE BONDING USING BLUSH LACQUER

This is a division of application Ser. No. 482,436, filed June 24, 1974, now U.S. Pat. No. 3,938,659.

This invention relates to bonding two surfaces together, particularly to form packages for sterilized material. More particularly, this invention relates to frangible bonds formed by respective layers of dried blush lacquer and adhesive material and to their method of manufacture and to products made therefrom wherein the bonds may be broken by forces rupturing the cohesive bonds within the blush lacquer.

In the packaging of pharmaceutical products such as sterile surgeon's gloves, masks, surgical dressings and surgical kits, it is common to seal the product between two sheets of paper or between a sheet of paper and a sheet of clear film or a plastic tray. The product thus packaged is then sterilized and sent to the customer as a sterile product. The exterior of the package must be considered contaminated, and it is therefore important that the product be removed without contamination from the exterior of the package. For this reason, the practice has been adopted of making a package that is opened by peeling as opposed to simply tearing the paper, which would shower the sterile contents with bacteria.

One manner of forming a peelable package has been to use a rubber cohesive peeling system with rubber bonds that were ruptured upon peeling. A substantial difficulty with this arrangement has been that the sealing system was resealable, making it possible that the package be opened or partly opened and thereafter resealed after the contents were no longer sterile. As it is important that once the product is sterilized its sterility may be depended upon, it is preferable that it be made impossible to reseal by merely reclosing the package. To preclude such resealing, it has been common to utilize so-called heat seal resins wherein the heat seal material is heated to bond the two surfaces together, forming bonds which upon rupture do not reseal merely by forcing the two surfaces back together. On the other hand, a substantial difficulty with the heat seal arrangement has been that when the heat seal bonds were reliably formed, their rupture resulted in picking fibers from the paper utilized to form the package. Such fiber picking made contamination possible if not certain.

Therefore, in accordance with the present invention, a dried blush lacquer is utilized in conjunction with a layer of adhesive material to produce bonds that rupture through the blush lacquer without picking fibers from the paper.

A blush lacquer may be defined as a coating composition comprising a film-forming resin dissolved in a vehicle composed of a blend of a solvent and a non-solvent for the resin and which forms its final coating merely by evaporation of the vehicle, with the solvent evaporating ahead of the non-solvent. The solvent and non-solvent may each be one or more liquids. The solvent is more volatile than the non-solvent, so that upon application of the blush lacquer to a substrate and subsequent evaporation of both the solvent and non-solvent therefrom, the dried blush lacquer forms a layer with voids and discontinuities therein due to the prior evaporation of the solvent with the prolonged retention of the less volatile non-solvent. The layer may be in the form of fibrils of resin forming a network of resin where the fibrils are more or less independent of one another, the degree of independence determining the cohesive strength of the layer. The film-forming quality of the resin provides tensile strength to the fibrils. The dried blush lacquer is normally opalescent to opaque in appearance.

In accordance with the present invention, a peelable bonding system is formed by disposing a blush lacquer on a paper or other substrate, evaporating the solvent and non-solvent from the coating, and overlaying the dried lacquer with adhesive material, preferably heat seal material, that is, material bonding upon the application of heat. A cover layer, such as a plastic film, is then overlaid, and caused to adhere to the blush lacquer, as by the application of heat in suitable areas to cause the heat seal material to form a bond between the blush lacquer and the cover layer. The materials and concentrations used assure that the cohesive internal bonds of the blush lacquer form the weakest link in the bonding system. Under such conditions, the cohesive bonds of the blush lacquer rupture prior to the rupture of the internal bonds of heat seal material or the bonds between the heat seal material and the cover layer, between the heat seal material and the blush lacquer and between the blush lacquer and the substrate. Further, the internal cohesive bonds of the blush lacquer are weaker than the internal bonds of the substrate and cover layer. Under these circumstances, the overall system bonding the cover layer to the substrate ruptures internally of the blush lacquer, assuring no picking of fibers from either the substrate or the cover layer and hence assuring sterility of the product contained between the substrate and the cover layer.

It is therefore an object of the present invention to provide a bonding system formed of a layer of dried blush lacquer and adhesive material, particularly heat seal material. It is a further object of the invention to form a package sealed by such bonding system and more particularly such package that may be sterilized. It is a further object of the invention to provide a sterilized package wherein the package is sealed by a seal formed of a blush lacquer and a heat seal material, wherein the package is opened by rupturing the internal cohesive bonds of the blush lacquer without packing fibers from the packaging material. Other objects and advantages of the invention will be apparent from the following detailed description particularly when taken in conjunction with the accompanying drawings in which:

Figure 1:
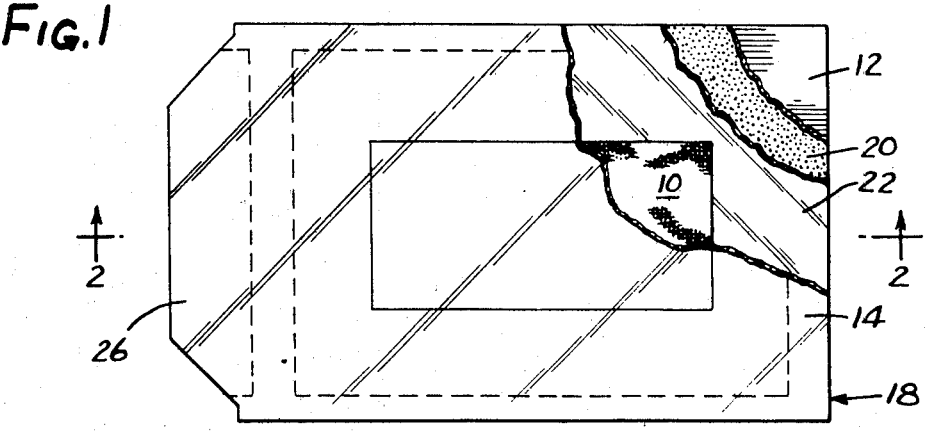
FIG. 1 is a plan view, partially broken away, of a sterilized package made in accordance with the present invention.
Figure 2:
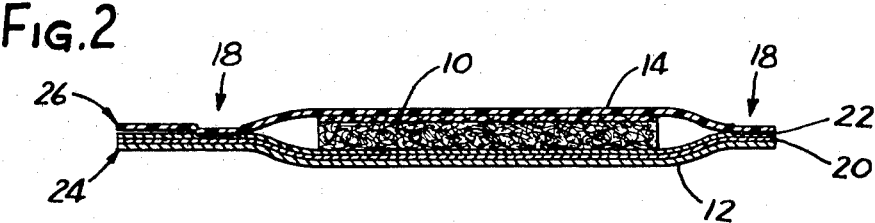
FIG. 2 is a cross sectional view of the package illustrated in FIG. 1, taken along line 2—2 of FIG. 1.
Figure 3:
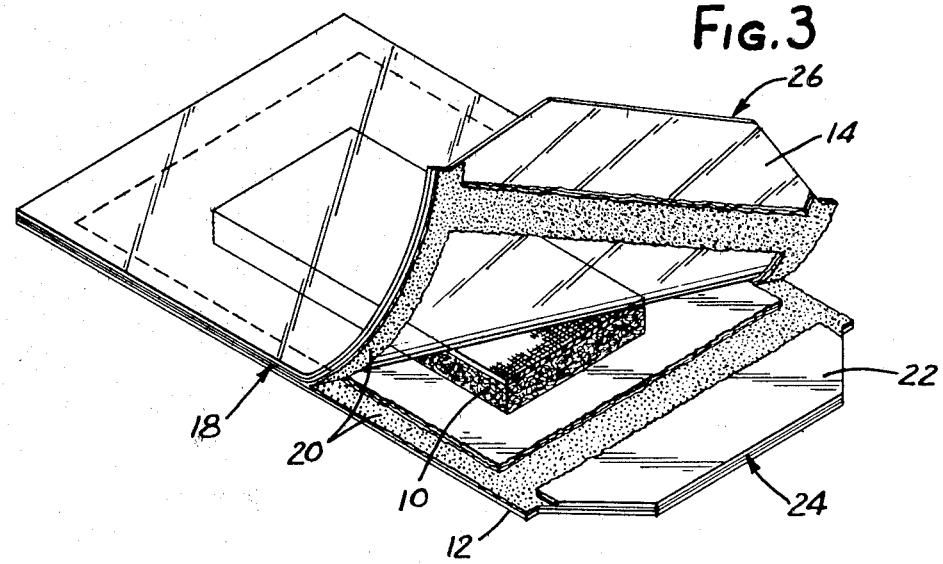
FIG. 3 is an isometric view of the package illustrated in FIG. 1, with the package partially opened.

FIGS. 1, 2 and 3 illustrate a sterile pharmaceutical package containing a surgical dressing 10. The package is formed by a paper substrate 12 and a plastic cover layer or closure member 14 between which the surgical dressing is disposed. The paper substrate and plastic cover layer are bonded together by a bonding system 18 disposed around the surgical dressing 10 between the paper substrate 12 and the plastic cover layer 14. The bonding system 18 is formed by a blush lacquer layer 20 and a layer of heat seal material 22.

The bond is formed by first laying the blush lacquer 20 on the paper substrate 12 and drying it. The blush lacquer may be applied uniformly over the entire surface of the paper substrate, or it may be laid in a pattern, as will be discussed further below in connection with FIG. 4. Then the heat seal material 22 is overlaid on the dried blush lacquer 20, the blush lacquer isolating the heat seal material from the substrate 12. The heat seal material, too, may be laid over the entire surface as shown or in a pattern, as will be discussed further below in connection with FIG. 4. The surgical dressing 10 is then placed on the coated substrate and overlaid with the plastic cover layer 14. Heat is then applied about the periphery of the package to bond the heat seal material 22 to the cover layer 14, thus bonding the cover layer to the substrate in the heated areas and sealing the dressing within the package. The heat sealing may be performed in a conventional and well-known manner, as by the use of a heated roller die. The die is designed to form a seal line which closes the package completely to provide a hermetically sealed unit.

The paper substrate 12 and the plastic cover layer 14 may extend beyond the seal line to form respective pull tabs 24 and 26 for opening the package.

With the package thus formed about the surgical dressing, the assemblage may be sterilized in a conventional manner as by autoclaving or flushing with ethylene oxide. The package may then be sent to hospitals or supply houses with the sterility of the dressing assured.

To gain access to the sterile dressing, the user pulls on the two tabs, as shown more particularly in FIG. 3, to rupture the cohesive internal bonds of the blush lacquer. As these cohesive bonds are weaker than any of the other internal bonds in the package or any of the other bonds between the cover layer 14 and the substrate 12, the rupture of the bonding system 18 is entirely internal of the blush lacquer layer, hence avoiding picking of any fibers from the substrate. Beyond the bonding system 18, the heat seal layer itself ruptures, leaving the heat seal material attached to the layer of blush lacquer, as illustrated.

It is, of course, important to be assured that the seal was adequately formed in the first place. In certain prior art seals, the effectiveness of the seal was evidenced by the pulling of fibers from the substrates. As this is one of the circumstances it is desired to avoid, identification of adequate sealing is here afforded by placing a dye in the blush lacquer to form a colored telltale. Thus, when the coating is ruptured, the transfer of dye to the cover layer indicates that the seal was previously complete.

The material of the blush lacquer will not again seal when the two parts of the ruptured coating are forced together, hence precluding the possibility of resealing any package once opened. The user may then be assured that any package sealed when he gets it has remained sealed from the time of initial sealing, hence assuring sterility.

The present invention has been described particularly in a preferred embodiment for packaging pharmaceutical products. It has a number of other uses, and even in the packaging of pharmaceutical products there may be a number of variables depending, for example, upon the particular product being packaged and the manner in which it is desired to sterilize it. Although various modifications may be made in the package, the bonding system and their method of manufacture, certain materials and arrangements thereof have been found particularly suitable.

Although other substrates may be used, a substrate found particularly useful is paper. More particularly, a paper useful in packaging sterilized products is pharmaceutical kraft having a pinhole free Gurley porosity typically in the range of 65 to 150 seconds and a basis weight of 25 to 65 pounds (per ream of 3,000 square feet). It is preferable that such paper be made of strong, virgin fiber resistant to color reversion when sterilized. Depending upon the conditions to which the package is to be exposed and the use to which it is to be put, and particularly when the product is to be sterilized by steam, the paper is made water resistant, being given a high degree of wet strength and made relatively water repellent. The paper should have relatively strong interfiber bonds, especially on its surface. For packaging pharmaceutical products it is generally desirable that any surface sizing be non-nutritive so as not to feed bacteria. It is, however, desirable that the paper have some holdout qualities, such as may be achieved by sizing, so that the subsequent blush lacquer coating does not soak excessively into the paper.

The blush lacquer coating is critical to the invention; however, the particular materials that may be used are various, again depending upon the uses to which the product is to be put. Blush lacquers are well known in the art, and a number of them may be used in the present invention. As defined above, a blush lacquer is a coating composition comprising a film-forming resin dissolved in a vehicle composed of a solvent and a non-solvent for the resin, and it forms its final coating merely by the evaporation of the vehicle with the solvent evaporating ahead of the non-solvent. When the blush lacquer is dried, the solvent is evaporated first, forming fibrils of film-forming resin separated by the non-solvent. The subsequent evaporation of the non-solvent leaves the fibrils of resin. Film-forming implies structural tensile strength, the strength depending upon the particular film-forming resin used. Further, the strength of the resin network depends upon the amount of resin relative to the voids in the layer and upon the relative independence of the fibrils from one another. These, of course, depend upon the relative amount of non-solvent in the initial blush lacquer. Cellulose derived film-forming resins have been found particularly suitable, although vinyl or acrylic based film-forming resins may be used. Specifically, the film-forming resins may be, for example, nitrocellulose, cellulose acetate, cellulose acetate butyrate and cellulose acetate propionate.

The vehicle used in the blush lacquer depends, of course, on the film-forming resin used. The vehicle must include both a solvent and non-solvent for the resin. The solvent and non-solvent should be miscible. Alcohol and water, for example, have been used to cause blushing. The particular solvents and non-solvents depend not only on the relative non-solvency of the resin but on their relative evaporation rates. It is the solvent that must evaporate first so that the solid resin fibrils may be formed by the action of the non-solvent in producing voids in the precipitating resin. The necessary rates of evaporation are also determined in part by the conditions of manufacture, as, for example, the time available for drying under given conditions. Various suitable solvents for nitrocellulose and similar resins are acetone, methyl acetone, methyl ethyl ketone and methyl acetate. Suitable non-solvents include toluol, xylol and aliphatic hydrocarbons such as naphtha (V.M. & P.). Water may also be used.

The relative proportions of resin and solvent and non-solvent are determined in part by the desired strength of the ultimate product and the method of its production. This also determines in part how thick to apply the coating of blush lacquer. The resulting dried layer of film-forming resin must have the appropriate tensile strength assuring that the cohesive bonds of the film-forming resin fail first in the bonding system and any resulting package. The materials utilized must also be compatible with the materials and environment to which it will be exposed in further processing and use.

The blush lacquer may be applied in a well-known fashion utilizing conventional paper-coating apparatus and techniques. It may be applied by printing, which includes the allover application of blush lacquer. The evaporation of the vehicle must proceed at a rate assuring the prior evaporation of the solvent. Fast evaporation is desirable for efficiency and rate of production, but evaporation must not be at such high temperature as to drive off the non-solvent prematurely. Generally satisfactory evaporation rates are obtained by passing the substrate with the blush lacquer thereon through a forced air oven operating at a high rate of air flow and a relatively low temperature. The high rate of air flow assures a relatively high rate of evaporation, while the temperature is kept low enough so as to assure the prior evaporation of the solvent. Particular temperatures depend upon the particular solvents and non-solvents used. On the other hand, as mentioned above, the particular solvents and non-solvents may depend in part upon the drying methods and apparatus available. The substrate is preferably passed continuously through a relatively long oven in a continuous operation.

As mentioned earlier, a preferred adhesive coating is heat seal material. Various heat seal materials may be utilized, and indeed the heat seal material may form the cover layer of the package, making a separate element unnecessary. The heat seal material may be applied as hot melt to the surface of the dry blush lacquer, or it may be applied in solution or suspension and precipitated upon the evaporation of a vehicle. A particular heat seal material that has been found efficacious is ethylene vinyl acetate precipitated upon the evaporation of its vehicle. A vehicle found useful has been the combination of toluol and aliphatic hydrocarbons. As may be noted, the vehicle for the heat seal material of this example was included in the examples of the non-solvent part of the vehicle for the blush lacquer; it therefore does not dissolve the dried blush lacquer of those examples. It is essential that the solvent used in forming the layer of heat seal material not materially attack the dried blush lacquer to which it is applied. Ethylene vinyl acetate is a preferred heat seal material, as it forms a layer that is peculiarly suitable for gas sterilization, for in thin layers it forms a relatively poor barrier to ethylene oxide as conventionally used for sterilizing in a carrier of hydrocarbons. Thus, when the completed package is subjected to ethylene oxide sterilization, the ethylene oxide penetrates not only the porous paper substrate and the resin network of the blush lacquer but also the heat seal coating. At the same time ethylene vinyl acetate is not attacked by the ethylene oxide. Other heat seal materials may be more suitable for autoclaving where it is important that the high temperature steam not attack the heat seal material, as by softening or completely melting it.

When the layer of heat seal material is applied over all the blush lacquer layer and the enclosed product 10 is between the cover layer and the heat seal layer, the heat seal layer is made thin enough and weak enough so as to fail following rupture of the bonding system 18. Otherwise, the heat seal material would merely peel from the blush lacquer, leaving the product still enclosed between the heat seal material and the cover layer.

The cover layer may also take a number of forms. It may, for example, be the same paper as for substrate. In fact, depending upon the packaging operation used, the substrate with the blush lacquer and heat seal material thereon may be used as a unit to form the cover layer, with the two layers of heat seal material juxtaposed. This may be achieved by folding a single sheet. As mentioned above, it is also possible that the heat seal layer itself form all or part of the cover layer. To form part of the cover layer, the heat seal material may be applied to a paper cover layer substrate and then heated to seal the cover layer to the blush lacquer layer to form the sealed package. Commonly, the cover layer is a sheet of clear film or a clear plastic tray, permitting visual inspection of the article contained in the package. Suitable films are a laminate of polyethylene film and polyester film such as that sold by du Pont under the trademark Mylar, and a film of high density polypropylene. Nylon film or polyolefin film may also be used.

One particular product successfully used in forming a sterilizable pharmaceutical package utilized pinhole free pharmaceutical kraft paper having a basis weight of about 40 pounds (per ream of 3,000 square feet) and a Gurley porosity of about 80 to 90 seconds. Blush lacquer containing nitrocellulose was applied in a thick layer to produce a coating having a dry weight of 5.5 pounds per ream. The particular blush lacquer used was the product sold by Morton Chemical Company under the trademark Adcote 148-39A. The composition of such blush lacquer in weight percent was:

| | |
|---|---|
| Nitrocellulose | 22% |
| Acetone | 32% |
| Alcohol (95% ethanol) | 30% |
| Toluol | 8.7% |
| Naphtha (V.M. & P.) | 7.0% |

Water was added to increase opacity, and the product was thinned with acetone to a solid content of about 15%. It was applied to the paper substrate in a conventional paper-coating machine and dried by being run through a 40-foot oven at a rate of 300 feet per minute. The oven was a forced hot air oven providing a high rate of air flow. At the same time the temperature was limited to 150° to 175° F. to drive off the solvents and non-solvents at the appropriate rates, where first the solvents were driven off and then the non-solvents were evaporated by the time the coated paper had passed through the oven. A coating of ethylene vinyl acetate solution as sold by Morton Chemical Company under the trademark Adcote 33G1A was then applied and dried in a similar manner. The heat seal solution comprised ethyl vinyl acetate in a vehicle of toluol and aliphatic hydrocarbons. The concentration of ethyl vinyl acetate and the thickness of the applied layer produced a coating of heat seal material of 3 pounds per ream.

The coated paper thus formed was used to form a package as shown in the drawings with the thus coated paper utilized to form the cover layer 14. The resulting package was then sterilized in a conventional manner with ethylene oxide. The efficacy of the sterilization was established by subsequent testing of the contents of the package. Further, the resulting product was tested with a standard tensile testing apparatus, namely, an Instron tester. Using inch-wide strips of the heat seal structure to peel the cover layer from the substrate at a rate of 12 inches per minute required from 150 to 450 grams. Dye in the blush lacquer was transferred to the heat seal material, establishing that the seal had been properly made. Further, visual examination established that there was no pulling of fibers and that the bonding system failed by failure of the cohesive bonds within the blush lacquer layer.

Various modifications may be made in the product and its method of manufacture within the scope of the present invention. As mentioned above, the heat seal material or both the heat seal material and the blush lacquer may be applied in a pattern, leaving open areas. This is particularly useful in assuring that the package be sufficiently permeable to sterilizing gas. It also may conserve material.

Figure 4:
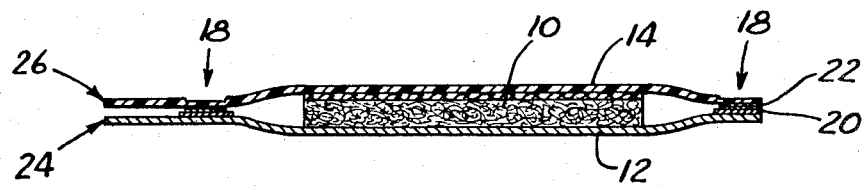
FIG. 4 is a cross sectional view of a package like that illustrated in FIG. 1 with patterned layers of blush lacquer and heat seal material.

One such patterned structure is illustrated in FIG. 4, wherein the blush lacquer layer 20 is deposited in a picture frame pattern, being placed substantially only at the bond 18, and the layer of heat seal material 22 is superposed in registry therewith. Such patterned structure is readily achieved by standard printing processes. Desirably, the area covered by the layer of blush lacquer extends beyond the corresponding layer of heat seal material to assure that the heat seal material is everywhere separated from the substrate 12 by the blush lacquer. If the heat seal material were to extend to the substrate, rupture of the blush lacquer would not separate the heat seal material from the substrate, and fibers might be pulled therefrom.

What is claimed is:

1. A product with frangible bonding including the combination of a paper substrate having internal bonds bonding it together internally, and a frangible bonding system, said frangible bonding system comprising a bonding agent in the form of a dried blush lacquer bonded to said substrate by interlayer bonds, and heat seal material for bonding said blush lacquer to a surface, said heat seal material having internal bonds bonding it together internally and being bonded to said blush lacquer by interlayer bonds, said dried blush lacquer being formed of film-forming resin containing voids, the film-forming resin forming cohesive internal bonds of said blush lacquer, said voids making said cohesive internal bonds of said blush lacquer weaker than the internal bonds of said substrate and said heat seal material and the interlayer bonds between said blush lacquer and said substrate and between said blush lacquer and said heat seal material.

2. A product according to claim 1 wherein said substrate is pharmaceutical kraft paper.

3. A product according to claim 1 wherein said paper is coated with non-nutritive surface sizing repellent of the vehicle with which the blush lacquer is applied.

* * * * *